United States Patent [19]

Revici

[11] Patent Number: 4,681,753

[45] Date of Patent: Jul. 21, 1987

[54] PHARMACEUTICAL COMPOSITIONS HAVING ANTINEOPLASTIC ACTIVITY

[75] Inventor: Emanuel Revici, New York, N.Y.

[73] Assignees: F.C.N.s.r.l., Bergamo, Italy; Alphatime Ltd, Berkhamsted, Great Britain

[21] Appl. No.: 585,855

[22] Filed: Mar. 2, 1984

[30] Foreign Application Priority Data

Mar. 8, 1983 [IT] Italy .............................. 19958 A/83

[51] Int. Cl.$^4$ ............................................. A61K 31/28
[52] U.S. Cl. ...................................... 424/10; 514/492
[58] Field of Search ........................... 424/10; 514/492

[56] References Cited

FOREIGN PATENT DOCUMENTS 0095663  7/1983  European Pat. Off. .

OTHER PUBLICATIONS

Chemical Abstracts 102:12367n, (1985).

Primary Examiner—Jerome D. Goldberg
Attorney, Agent, or Firm—Bucknam and Archer

[57]  ABSTRACT

Pharmaceutical compositions endowed with antineoplastic activities, containing bivalent negative selenium, for instance as diselenide; carboxylic acids, aldehydes or ketones having odd number of carbon atoms, and optionally poly alcohols, alcohols, aminoalcohols, corticosteroids, nicotinic acid, aminobenzoic acids.

8 Claims, No Drawings

PHARMACEUTICAL COMPOSITIONS HAVING ANTINEOPLASTIC ACTIVITY

The present invention refers to pharmaceutical composition having antineoplastic activity, containing as active principle a combination of the following compounds:

(a) bivalent negative selenium in form of selenium incorporated in "tung oil" or of diselenide of formula R—Se—Se—R, wherein R is an alkyl or alkenyl group having an odd number of carbon atoms;

(b) an aliphatic carboxylic acid, aldehyde or ketone having odd number of carbon atoms.

Another object of the invention is provided by pharmaceutical compositions containing, in addition to said compounds and to suitable excipients, also other agents endowed with complementary activities, synergistic or able to decrease the side effects.

The antitumoral and antineoplastic activity of selenium derivatives has been already described in the European patent application No. 83104923.4 of May 19, 1983 (publication No. 0095663).

From a pharmacological point of view, the compound obtained by reaction of elementary selenium and eleostearic acid (main constituent of tung oil), whose action can be enhanced by the contemporaneous administration of extracts of Bixa orellana seeds, proved to be particularly active.

It has now been found that the contemporaneous administration of carboxylic acids, aldehydes or ketones having an odd number of carbon atoms is able to decrease the side effects induced by selenium and allows therefore to increase the dosage.

Also substances such as alcohols or polyalcohols, some amine compounds and corticosteroids which turned out to be active in decreasing the side effects, can be optionally present in the compositions according to the invention.

Preferably, 3-heptanone, 3-pentanone, 3 or 5-nonanone, in combination with propyl, pentyl, heptyl, nonyl or undecyl diselenide, are used.

The composition according to the invention can also comprise lipophilic vehicles, such as sesame oil or the like. The relative proportions of the (a) and (b) constituents in the pharmaceutical compositions according to the invention may range from 1:10 to 1:50.

Other substances which can be present according to the invention are polyalcohols or alcohols having odd number of carbon atoms, preferably glycerol, aminoalcohols, nicotinic acid, aminobenzoic acids, cortisone.

Preferred composition comprise constituent (a) (diselenide) and ketone (b) (3-heptanone) in the weight proportions of 1:25 for the parenteral administration and of 1:40 for the oral one.

The diselenides according to the invention are prepared with known methods while for the preparation of the reaction product of elementary selenium and eleostearic acid or tung oil, reference is made to the previously cited European patent application.

As far as the compositions of the invention are concerned, the following, non limiting examples are reported.

EXAMPLE 1

Vials for intramuscular injection

Dipentyl diselenide: 2%
3-Heptanone: 50%
Sesame oil: 48%

The above composition is distributed into 1 ml vials to be administered by intramuscular route.

EXAMPLE 2

Gelatine capsules or drop for oral route

Dipentyl diselenide: 2%
3-Heptanone: 80%
Sesame oil: 18%

0.5–2 Ml of the above composition are dosed in gelatine capsules. Alternatively, the same composition can be directly administered as drops.

The acute and subacute toxicity of the composition of the Example 1 have been determined by the subcutaneous and intraperitoneal route in mice, rats and dogs.

Acute toxicity

The $LD_{50}$ of the composition of the Example 1, after administration both by subcutaneous and intraperitoneal route, in $FC_1$ mice (28–32 g) and in Carworth rats (150–170 g) proved always to be higher than 350 mg Se/kg or than 100 ml/kg.

Subacute toxicity

The subacute toxicity has been studied by administering the composition of the Example 1 by subcutaneous route to Carworth rats (150–170 g) for six weeks (5 days a week) at doses ranging from 10.5 to 350 mg/Se/kg or 3–100 ml/kg. No death was noticed in any group during treatment.

After the animals' sacrifice, 20 or 40 days after treatment, the microscopic, hematologic and hematochemical exams did not show any pathological change.

Subacute toxicity in dogs

Two groups of 6 Beagle dogs were treated with 0.60 and 1.26 ml/kg of the composition of Example 1 five days a week for five weeks. No death occurred. After sacrifice at the end of the treatment, the pathological and biochemical exams did not show any pathological change.

The compositions according to the invention exert an antineoplastic activity similar to those of the already mentioned european application, such activities being sometimes enhanced because of the high selenium dosages attainable with the compositions of the invention.

The compositions of the invention can be used in a variety of neoplastic conditions, at dosages ranging from 5–20 g by oral route and from 0.5 to 2 ml by intramuscular route, 2 to 4 times daily.

The treatment is based on the concept of a primary subnuclear anomaly and of an abnormal lipidic dualism: the number of eosinophils in blood, the pH, the specific gravity and the surface tension are the most important guide parameters for the treatment.

(The concept of anabolic-catabolic dualism, and relative definitions, are widely illustrated—also from an experimental point of view (in animal field)—in E. Revici, *Research in Physiopathology*, ediz. Van Nostrand, Princeton, 1961). Nevertheless, the validity of the invention should not be considered as based on the actual verification of the theoretical considerations discussed in said treatise.

I claim:

1. A pharmaceutical composition which comprises an effective amount of as the active principle, a combination of:

component (a) which is a diselenide of formula R—Se—Se—R, which is dipropyl, dipentyl, dipheptyl, dinonyl or diundecyl diselenide and component (b) which is 3-heptanone, 3-pentanone or 5-nonanone, said components (a) and (b) being present in proportions ranging from 1:10 and 1:50, respectively, and a lipophilic vehicle.

2. A composition according to claim 1 which additionally contains at least one member selected from the group consisting of alcohols with odd number of carbon atoms, polyalcohols, glycerol, aminoalcohols, nicotinic acid, aminobenzoic acids and corticosteroids.

3. The composition according to claim 1 wherein said lipophilic vehicle is sesame oil.

4. A pharmaceutical composition according to claim 1 containing dipentyl diselenide and 3-heptanone in proportions ranging from 1:10 to 1:50.

5. A pharmaceutical composition according to claim 1 which contains 2% dipentyl selenide as component (a) and 80% 3-heptanone as component (b) and which is suitable for oral administration.

6. The composition according to claim 5 in unit dosage form which contains 5–20 grams per unit.

7. A pharmaceutical composition according to claim 1 suitable for parenteral administration which contains 2% dipentyl selenide and 50% 3-heptanone.

8. The composition according to claim 7 in unit dosage form which contains 0.5–2 ml per unit.

* * * * *